United States Patent [19]

Foley

[11] Patent Number: 4,584,281

[45] Date of Patent: Apr. 22, 1986

[54] CONTROLLED DELIVERY OF IMMISCIBLE MATERIALS INTO AN AQUEOUS SYSTEM

[75] Inventor: Lary L. Foley, San Francisco, Calif.

[73] Assignee: The Clorox Company, Oakland, Calif.

[21] Appl. No.: 581,146

[22] Filed: Mar. 23, 1984

Related U.S. Application Data

[62] Division of Ser. No. 303,472, Sep. 18, 1981, Pat. No. 4,440,542.

[51] Int. Cl.$^4$ ............................................. C04B 38/00
[52] U.S. Cl. ........................................ 501/85; 501/12; 501/39; 106/75
[58] Field of Search ............................ 501/85, 39, 12; 252/378 R; 106/75

[56] References Cited

U.S. PATENT DOCUMENTS

| | | | |
|---|---|---|---|
| 3,450,547 | 6/1969 | Sams et al. | 106/75 |
| 3,743,601 | 7/1973 | Rao et al. | 106/75 X |
| 4,401,586 | 8/1983 | Ghiringhelli | 501/85 X |

FOREIGN PATENT DOCUMENTS

| | | | |
|---|---|---|---|
| 49-113814 | 10/1974 | Japan | 106/75 |
| 178726 | 1/1966 | U.S.S.R. | 501/85 |

*Primary Examiner*—William R. Dixon, Jr.
*Assistant Examiner*—Steven Capella
*Attorney, Agent, or Firm*—S. M. Westbrook; J. J. Hayashida

[57] ABSTRACT

Immiscible components are controllably released into aqueous systems by impregnating silica-silicate open cell foams with the immiscible components. As the silica-silicate foams are gradually dissolved, the immiscible components are released. Fragrance oils and dyes are particularly adaptable for use in the invention. In fact, silica-silicate foams impregnated with fragrance oils having polar functional groups, exhibit an unexpectedly slower rate of dissolution into aqueous environments and consequently, fragrance oils and dyes admixed therewith are released in aqueous systems over extended time periods.

3 Claims, No Drawings

CONTROLLED DELIVERY OF IMMISCIBLE MATERIALS INTO AN AQUEOUS SYSTEM

This is a divisional application of co-pending application Ser. No. 303,472, filed Sept. 18, 1981, now U.S. Pat. No. 4,440,542.

FIELD OF THE INVENTION

Materials normally insoluble and immiscible in aqueous systems may be released in a controlled manner into such systems by adsorbing and trapping the materials on and into the interstices of a water-soluble inorganic foamed structure i.e., a silica-silicate foam. As the foamed structure slowly dissolves into the aqueous environment, the absorbed and trapped materials are concurrently released.

BACKGROUND OF THE INVENTION

In the treatment of aqueous systems with sanitizing and/or bacteriostatic, or surface active agents, it is very often desirable, especially in the consumer products markets, to also impart aesthetically pleasing components, such as fragrances and colorants into the system. An illustration of such a system is the treatment of flushing toilets with automatically dispensed sanitizing, cleansing, and bacteriostatic agents to effectively clean and sanitize the toilet bowl with every flush. From an aesthetic standpoint, it has been found desirable to dispense fragrances and colorants at the same time, to impart pleasing fragrance to the environment. The colorants not only impart a pleasing appearance to the water in the toilet bowl, but they may also serve to assure the consumer that, in fact, the desired treating agents (which are normally colorless) are being dispensed. The colorants may also serve as an indicator that the dispensing package has been exhausted, i.e., their absence indicates the necessity for renewing the treatment agents.

Most fragrances are hydrophobic in nature and are ordinarily formulated and/or preserved in organic hydrocarbon bases. These "oily, waxy" bases are also hydrophobic and only contribute to the aqueous insolubility of the fragrance oils.

On the other hand, the systems of interest are aqueous in nature, and it therefore becomes a problem to assure uniform and steady dispersion of the fragrance and, very often, the colorant components on a continuing basis throughout the aqueous medium.

Heretofore, the dispensing of the water immiscible components into the aqueous medium has been solved by providing separate reservoirs for the immiscible components. These reservoirs have been provided with some type of valving arrangement to meter predetermined quantities of the immiscible components into the aqueous medium during periods of aqueous flow or agitation. Upon release, the immiscible components are physically carried along with the water flow, float to the surface at quiescent portions of the system, where they are released or evaporated into surrounding environment.

Such separate reservoir, valving arrangements suffer from a number of potential defects. First, since the immiscible component is released on a "shot by shot" basis, sufficient material must be released on each "shot" to ensure that enough material is delivered to the system to provide the desired component at remote locations from the reservoir valve location. This requirement demands release of a certain quantity of component at each operation of the valve. The mechanics of this operation, frequently requires the release of excess quantitites of the components and the provision of relatively large reservoirs. This process also tends to be inefficient and often requires the release of larger "shots" of component than necessary to accomplish the job.

Secondly, the intermittent operation of the valves requires some type of sensing mechanism to ensure valve operation at the proper time. Such sensing mechanisms and the valves themselves are subject to failure or faulty operation.

Thirdly, since sophisticated sensing and valve mechanisms are costly, there is a tendency to use the less precise and less complicated mechanisms, whereby, close control of the amount of immiscible component is unable to be maintained. The result is poor control over the uniform release of the immiscible components; and attendant greater use of components than is necessary for optimum results.

Thus it is apparent that there is a need for a simple reliable mechanism that will deliver closely controlled amounts of immiscible materials into an aqueous system.

BRIEF DESCRIPTION OF THE INVENTION

The present invention utilizes silica-silicate foams to facilitate the delivery of immiscible components into aqueous systems in a controlled manner with excellent efficiency and reliability. The immiscible components are adsorbed onto the foam and trapped within the voids which are inherent to the foam's structure. Silica-silicate foams are water-soluble, and as the foam dissolves when contacted with an aqueous system, the adsorbed and trapped immiscible components are released.

Although the foams are water-soluble it is important to note that their solubility is inherently lowered when the immiscible components are adsorbed thereon. That is, the ordinary low water solubility of the foam is greatly decreased and retarded by the presence of the adsorbed components coating the foam surfaces. Thus there is a synergistic effect of prolonging the dissolution of the silica-silicate foam in the aqueous environment and the concomitant prolonged release of the immiscible components into the same system.

The rate of release of the immiscible components is also controlled by several characteristics of the foam composition. Variations in the silica to silicate ratios affects the rate of solubility of the foam in water; and the density of the foam also affects the rate of dissolution in the aqueous environment. Therefore, proper selection of silica-silicate ratios, foam density and the immiscible components themselves determine the rate of release of the immiscible components into the aqueous system.

More specifically, finely divided silica and silicate solution, preferably sodium silicate, are mixed together with added water to form a gel-like composition. This gel is then subjected to heat energy, such as from a microwave generator. Under the influence of the energy input, water is driven from the silica-silicate reaction product and the silica-silicate product swells, foams and solidifies into a porous, rigid solid.

The solid foam is then impregnated with a liquid solution of the desired immiscible component, ordinarily comprising organic components dissolved in an oil, or an oil-like base. The organic component-oil solution is adsorbed onto the silica-silicate and additional quantities thereof are trapped within the voids throughout the foam structure.

The impregnated foam product may then be placed in an aqueous system, whereupon the foam is gradually dissolved and the accompanying immiscible components are slowly and evenly released into the aqueous surroundings.

The silica-silicate foam is especially useful in regulating the slow and prolonged release of fragrance oils into an aqueous system in which such fragrance oils are normally immiscible.

It is therefore an object of the invention to provide a silica-silicate foam impregnated with water immiscible components.

It is another object of the invention to provide a method for the slow and prolonged release of immiscible components into an aqueous system.

It is still another object to provide a method for the slow and prolonged release of immiscible fragrance oils into an aqueous system.

It is yet another object of the invention to provide a silica-silicate foam impregnated with water immiscible organic components and to immerse said impregnated foam over extended periods of time in an aqueous environment whereby said foam slowly dissolves and thereby releases the organic components into the environment over said extended time periods.

Other objects and advantages of the invention will become apparent from a review of the following disclosure and the claims appended hereto.

DETAILED DESCRIPTION OF THE INVENTION

A rigid, water soluble foam is produced from mixing together suitable quantities of finely divided silica and sodium silicate solution, along with added water, if necessary, to form a gel, or gel-like product. The silica-silicate gel is then strongly heated, as by means of microwave energy, to drive off a quantity of the water. As the water is driven off, the gel expands (intumesces) and hardens to form the desired foam.

More specifically, silica, which is silicon oxide, $SiO_2$, is secured from any of a number of industrial souces as a very fine anhydrous powder. Such sources are, for instance, the Cabot Corporation, of Boston, Mass.; or the Philadelphia Quartz Corporation of Valley Forge, Pa. The silica powder is a standard article of commerce commonly used in the manufacture of glass, ceramics, refractories, abrasives, enamels; for the decolorizing and purification of oils, and other petroleum products; and as a component in scouring and grinding compounds, ferro-silicon, and as casting molds. The powder has an extremely low coefficient of expansion by heat; and is essentially insoluble in water or acids, with the exception of hydrofluoric acid.

The standard commercial product, which can be obtained in very high purity, i.e., essentially 100% $SiO_2$, is entirely suitable for use in the present invention.

The sodium silicate is the reaction product of sodium oxide, $Na_2O$, and silica. It is available either as an aqueous solution, or as a powdered product. The sodium silicate component of the gel is a standard article of commerce and may readily be obtained from several sources, e.g., the Philadelphia Quartz Corporation of Valley Forge, Pa. While powdered silicate may be used to prepare the gel, it is much more economical and convenient to use aqueous solutions of sodium silicate.

These aqueous solutions are obtainable in varying composition with respect to the ratio between sodium and silica, as well as in various densities. The solution, for instance, which is most commonly available contains about 40% by weight $Na_2Si_3O_7$. If desired, other silicate solutions, such as $Na_2SiO_3$, or $Na_6Si_2O_7$ may also be utilized. The desired properties, i.e., solubility, foam density, etc. of the final foam product, will generally determine the particular silicate solution utilized as a starting material.

As will be discussed hereafter, the physical and chemical properties of the silica-silicate foam depends, in great measure, upon the ratios of sodium oxide ($Na_2O$), Silica ($SiO_2$), and water present in the gel before the heating procedure. An improper balance will result in weak, friable foams, which quickly disintegrate when placed in the aqueous systems; or heavy foams of poor porosity that are incapable of adsorbing sufficient quantities of the immiscible component. Thus the particular silicate solutions utilized are selected with consideration for the properties of the foams resulting from their use.

In any event, silica powder is slowly added with stirring to the selected silicate solution along with a sufficient amount of deionized water to produce a gel, or gel-like product. The viscosity of the resulting gel is determined by the original viscosity of the silicate solution, by the amount of silica powder added, and by the amount of water added. The viscosity of the gel product increases with increasing silica; but decreases with increasing water. Thus it will be readily apparent that the final viscosity of the gel product can be easily controlled by varying the amounts of silica and water added to the silicate solution.

In order to produce a final foam product of sufficient strength to resist damage when handled, and at the same time of sufficient porosity to adsorb and retain the desired amounts of the organic components, it has been determined that gels having a composition of about 70–75% by weight water, about 20–25% by weight silica, and about 3–5% by weight sodium silicate, are necessary. In the instance where fragrance oils are to be adsorbed, it is desirable for the resultant foam to about 70 to 80% by volume porosity. In order to resist crushing and damage and to maintain its integrity during the extended period when being dissolved in the aqueous systems, it is also desirable that the foam product exhibits a minimum crushing strength of about 9–10 kg/cm$^2$. The above noted proportions of water, silica, and silicate, along with a final gel viscosity of about 12 to 20 Mcps., will produce foams of the required porosity and crush strength.

It will be understood that, under certain circumstances, e.g., the use of different immiscible components, or in an environment where the assurance of extended release of the immiscible component is not so critical, the foam strengths and porosities may be varied considerably from those which have been found to be desirable for the controlled, prolonged release of fragrance oils.

The gel is placed in a suitable mold within a microwave oven. Power is then applied, whereupon microwave energy is directed into the gel mass. Good energy coupling is achieved due to the presence of water. Depending upon the amount of gel present, microwave energy inputs in the 900 to 3000 watt range are sufficient to drive off water at a rate to cause the gel to foam up and expand to many times its initial volume and form extensive voids within the mass.

Heating is continued until good foam growth is observed. Perhaps some 80 to 90% or more by weight of the water originally present in the gel is driven off during the heating process. The resultant rigid, porous foam is then removed from the microwave oven and is allowed to cool. It is then ready for impregnation with the immiscible component.

The preferred foam has a porosity of at least 70% by volume or better with an open cell structure. That is, the voids should be open one to the other and not closed. The presence of an appreciable quantity of closed cells is undesirable.

As noted above, foams with a crush strength of about 9–10 Kg/cm$^2$ are satisfactory for use.

The immiscible components are loaded into the silica-silicate foam in a relatively simple method. The objective is to saturate the foam and fill the void spaces completely as possible with the immiscible components. As noted above, the immiscible components are in the liquid form and constitute a hydrophobic oily base in which the active components, such as fragrances or dyes are dissolved. Such materials generally have the viscosity of light mineral oils with a viscosity somewhat higher than water, but still quite fluid.

To ensure complete saturation of the silica-silicate foam, a vacuum procedure is appropriate. Specifically, the silica-silicate foam, in the form of blocks, is placed in a vacuum chamber equipped with suitable piping and valve means to afford the introduction of the immiscible liquid materials when desired. A mild vacuum is pulled on the foam blocks to reduce the air pressure within the voids. The liquid immiscible materials are then valved into the chamber to a level sufficient to cover the foam blocks. The chamber is then let up to atmospheric pressure and the immiscible components are thereby forced into the interior voids of the silica-silicate foam.

After a time sufficient to ensure thorough saturation of the foam, the blocks are removed from the vacuum chamber, and placed on a porous surface to permit drainage of the excess immiscible liquid. The foam is thoroughly "wet" by the immiscible components and the voids are saturated therewith. At this time the impregnated foam is ready for use, or the blocks can be sealed in a closed package until ready for use.

When desired, the impregnated foam blocks may be placed in the aqueous system into which the immiscible components are to be dispensed. A typical system is the tank compartment of a toilet where it is desirable to dispense disinfecting and/or detergent materials, as well as fragrances and to indicate the presence of the disinfectants/detergents in the flush water. The foam product may be utilized in conjunction with means to dispense disinfecting and/or detergent materials into the system, however, such disinfectant/detergent dispensing means forms no part of this invention.

The impregnated foam block, however, may be packaged along with the disinfecting/detergent materials as a unitary package; or it may be packaged separately from the disinfecting and detergent components. In any event, the impregnated foam block is placed within the tank compartment into contact with the flush water.

When in contact with the aqueous environment, the foam is subjected to the solvent action of the water. A silica-silicate foam having the typical chemical and physical characteristics noted above, when unimpregnated with the oily immiscible components will readily disintegrate and dissolve in the aqueous environment in a matter of a few hours. However, when impregnated with oily immiscible components, the dissolution and disintegration is drastically retarded and is extended to days or several weeks. Even more surprisingly, when the silica-silicate foams are impregnated with fragrance oils, the dissolution is even further extended to the order of several months.

For instance, utilizing identical size pieces of silica-silicate foam prepared from gels of identical composition and utilizing the same heating parameters, it has been noted that the unimpregnated foams dissolve and disintegrate in a matter of a day or two. When the foams were impregnated with a light hydrocarbon oil, disintegration occurred in a matter of several weeks. However, when the foams were impregnated with a fragrance oil e.g. Firminich disintegration was delayed for eight weeks and even longer. It should be understood that, in all instances, the foams disintegrated and dissolved. But in the instance of impregnation with immiscible fragrance oils, dissolution was delayed. Even though the foam decreased in size during dissolution, the remaining foam maintained its integrity.

It is believed that the extended dissolution and maintenance of integrity of the fragrance oil impregnated foams can be explained on the following basis:

Fragrance oils almost universally include functional groups which are capable of forming polar bonds. These polar functional groups therefore have the ability to associate rather strongly with the silica-silicate structure. When adsorbed on the silica-silicate surfaces the polar groups are associated strongly thereto, and the hydrophobic functional groups form a layer which protects the silica-silicate from ready contact with the water molecules which would dissolve the silica-silicate.

Eventually the fragrance oils slowly dissipate into the aqueous environment through diffusion. At any point of exposure, the silicate structure is attacked and dissolved by the water with attendant disintegration of the silica-silicate structure and additional release of the immiscible fragrance oils.

While the above explanation is believed to account for the increased stability of the silica-silicate foams impregnated with water immiscible polar compounds, its veracity is unsubstantiated and the explanation should be considered as theory only. In fact, however, tests have clearly shown that the integrity of silica-silicate foams is prolonged in an aqueous environment when the foams are impregnated with fragrance oils.

As a consequence of the increased life of the foams, the release of fragrance oils into the aqueous system is also prolonged over times far longer than normally expected from the amounts of fragrance oils utilized.

Dyes may also be added to the immiscible components to indicate the release therewith as the silica-silicate foams dissolve. The dye will be released at the same time the immiscible component is released. Thus the flush water will be dyed to indicate the presence of the desired disinfectants and/or detergents, when the release of the immiscible components is coordinated with release of the disinfectants/detergents.

Suitable fragrance oils for use in the invention are:

Citronellol, hydroxycitronellol, rhodinol, eugenol, geraniol, rose oil, heliotropine, peru balsam, ylang-ylang oil, isoeugenol, bergamot, coumarin, and any of the synthetic counterparts or blends of the foregoing, and odorant chemicals of which there is no counterpart in nature. Any or all of these materials may be used in combination to achieve any desired fragrance and odor counteractant effect.

Some fragrance oils found to be particularly useful in toilet flushing aqueous systems are: An herbal scent, Firminich 43.312/B; a fantasy scent, Firminich Cetylia Base ®; a lemon scent, Naarden 802605; and a pine scent, Synfleur C-78-132.

Suitable dyes for admixing with the fragrance oils are:

Acid Blue #9 (preferred); Acid Blue #1; Acid Blue #7; and Acid Blue #86.

As noted above, microwave energy is the preferred means of driving water from the silica-silicate gels. Microwaves will heat the gel throughout its entire mass virtually simultaneously, thus driving off water from the interior portions of the gel mass as well as from the exterior portions thereof. A uniformly open-celled fine foam structure may be therefor obtained.

The following examples will further illustrate various aspects of the invention:

EXAMPLE 1

The following table presents chemical and physical properties from typical experimental foam preparations:

TABLE I

| Sample # | Composition of Gel % W | | | Gel Viscosity Mcp. |
| --- | --- | --- | --- | --- |
| | Water | Silica | Na$_2$O | |
| A | 75 | 21.6 | 3.4 | 17.6 |
| B | 75 | 20.7 | 4.3 | 5.7 |
| C | 75 | 20.7 | 4.3 | — |
| D | 70 | 25 | 5 | 10.6 |

TABLE I-continued

| Sample # | Porosity % V | Strength, Kg/cm$^2$ |
| --- | --- | --- |
| A | 79 | 13.9 |
| B | 78 | 17.8 |
| C | 76 | 11.5 |
| D | 77 | 8.6 |

EXAMPLE 2

A silica-silicate foam tablet was prepared according to the above description. The tablet was impregnated with 30% by weight of the fragrance oil Cetylia, from Firminich. The impregnated tablet was placed into a laboratory flush system along with a quantity of calcium hypochlorite. As the system was repeatedly flushed, both the hypochlorite and the foam gradually dissolved into the water in the bowl. The hypochlorite, of course, normally gives a typical "chlorine" odor and the system was observed to determine if the released fragrance oil would mask the "chlorine" odor. After 100 flushes in which hypochlorite reached levels equivalent to 1.5 ppm chlorine, the Cetylia oil continued to strongly mask any "chlorine" odor. The remaining foam tablet was also intact and fragrance was still being released into the system.

I claim:

1. A method of producing a water soluble foam structure from an aqueous gel including silica-silicate and about 70 to 75% by weight water comprising driving a portion of said water off from the aqueous gel by applying microwave energy to said gel to thereby produce a foamed structure.

2. A silica-silicate gel for use in producing a foamed structure comprising from about 70 to 75% by weight water, from about 20 to 25% by weight silica, and from about 3 to 5% by weight sodium silicate.

3. The silica-silicate gel by claim 2 having a viscosity of about 12 to 20 Mcps.

* * * * *